United States Patent [19]

Ishimura et al.

[11] Patent Number: 4,942,261

[45] Date of Patent: Jul. 17, 1990

[54] PROCESS FOR PREPARATION OF ALLYL TYPE AMINE

[75] Inventors: Yoshimasa Ishimura; Takami Oe; Yuseki Suyama; Nobuyuki Nagato, all of Kawasaki, Japan

[73] Assignee: Showa Denko Kabushiki Kaisha, Tokyo, Japan

[21] Appl. No.: 282,095

[22] Filed: Dec. 9, 1988

[30] Foreign Application Priority Data

Dec. 11, 1987 [JP] Japan .................. 62-312339
Dec. 23, 1987 [JP] Japan .................. 62-323833

[51] Int. Cl.$^5$ .......................... C07C 209/16
[52] U.S. Cl. .................. 564/480; 564/319; 564/383; 564/386; 564/447; 544/358; 546/203; 546/205
[58] Field of Search .............. 564/480, 319, 383, 447

[56] References Cited

U.S. PATENT DOCUMENTS 4,120,901 10/1978 Hobbs et al. .................. 564/485
4,417,074 11/1983 Daughenbaugh et al. ......... 564/479

OTHER PUBLICATIONS

Research Disclosure 16906, p. 35, May 1978.

*Primary Examiner*—Glennon H. Hollrah
*Assistant Examiner*—Susan P. Treanor
*Attorney, Agent, or Firm*—Sughrue, Mion, Zinn, Macpeak & Seas

[57] ABSTRACT

An allyl type amine is prepared by reacting an allyl type alcohol represented by the following formula:

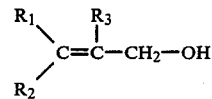

wherein $R_1$, $R_2$ and $R_3$ independently stand for a hydrogen atom, an aliphatic hydrocarbon group or alicyclic hydrocarbon having 1 to 8 carbon atoms, or an aromatic hydrocarbon group, with at least one member selected from the group consisting of ammonia, a primary amine and a secondary amine in the presence of a palladium compound and a multidentate phosphorus compound.

11 Claims, No Drawings

PROCESS FOR PREPARATION OF ALLYL TYPE AMINE

BACKGROUND OF THE INVENTION (1) Field of the Invention

The present invention relates to a process for the preparation of an allyl type amine. More particularly, the present invention relates to a process for the preparation of an allyl type amine which is broadly used as the starting material of a cationic polymer valuable as a coagulant or a medicine or agricultural chemical.

(2) Description of the Related Art

At the present, allylamine is prepared by reacting allyl chloride with ammonia (see U.S. Pat. No. 2,216,548 and U.S. Pat. No. 3,175,009). A process for preparing an allyl type amine by reacting a carboxylic acid ester of an allyl type unsaturated ether or allyl type unsaturated alcohol with ammonia in the presence of a combination catalyst comprising a palladium compound and a trivalent phosphorus or arsenic compound has been proposed (see Japanese Examined Patent Publication No. 49-20162). However, if allyl chloride or an allyl ester is used, hydrochloric acid or a carboxylic acid is produced with the synthesis of allylamine. Since this acid forms a salt with ammonia or the formed amine, the acid cannot be re-utilized. Moreover, in order to recover the amine, it is necessary to perform neutralization with an equimolar amount of a strong alkali. Furthermore, since a salt is formed, the process becomes complicated.

In the case where an allyl type alcohol is used as the starting material, water is formed as a by-product, and since this water does not react with the amine, the above-mentioned loss is not caused and the process becomes simple. However, the reactivity of the allyl alcohol is much lower than that of allyl chloride or the allyl ester. This can be confirmed from the difference between allyl acetate and allyl alcohol in the reactivity with dipropylamine shown in the following table (extracted from Research Disclosure, May 1978, page 35).

to palladium [Tetrahedron Letters, No. 43, pages 3821 to 3834 (1970)]. However, as pointed out hereinbefore, triphenylphosphine is gradually oxidized by allyl alcohol. Accordingly, precipitation of a black palladium compound is observed and the activity is not durable. This fact has been confirmed by experiments.

The reactivity of ammonia is lower than that of the amine, and none of catalysts are substantially effective for the reaction between allyl alcohol and ammonia. It has been confirmed that even if the reaction between allyl alcohol and ammonia is intended by using the catalyst of Atkins et al. under the same conditions, the reaction is hardly advanced. It also was found that if propylene glycol is used as the solvent and triphenylphosphine is added in excess, a yield of 6% is obtained by 2 hours' reaction, but deactivation of the catalyst is violent and further improvement of the yield is not attained. The reason is that oxidation of triphenylphosphine is caused, as pointed out hereinbefore. Accordingly, this catalyst system cannot be industrially used.

Furthermore, a process in which monoallylamine is synthesized from allyl alcohol and ammonia in the solid gas phase by using a phosphorus compound such as polyphosphoric acid as the catalyst has been proposed (see Japanese Unexamined Patent Publication No. 58-88342). However, also this process is defective in that the yield is poor and the practical utility is low.

As is apparent from the foregoing description, although the preparation of an allyl type amine by using an ally type alcohol as the allyl source is considered to be very advantageous, a process for preparing an allyl type amine by using an allyl type alcohol as the starting material, which can be industrially worked, is not established.

SUMMARY OF THE INVENTION

It is therefore a primary object of the present invention to provide a process in which an allyl type amine is prepared at a high selectivity by using an allyl type alcohol as the starting material.

More specifically, in accordance with the present invention, there is provided a process for the prepara-

| Solvent | Temperature | Catalyst | Allyl compound | Allyl Compound/Metal Ratio | Yield (%) of Allyl Amine Based on Starting Allyl Compound | Sampling Time (min.) |
|---|---|---|---|---|---|---|
| ethylene glycol | 35 | (allyl PdCl)$_2$/ 4(BuO)$_3$P | allyl acetate | 1942 | 99 | 30 |
| propylene glycol | 100 | (allyl PdCl)$_2$/ 4(BuO)$_3$P | allyl alcohol | 100 | 82 | 220 |

Although such conditions as the temperature, the allyl compound/catalyst molar ratio and the reaction time, adopted for allyl alcohol, are much advantageous over those adopted for allyl acetate, the yield is rather low in case of allyl alcohol even if the same catalyst is used. Thus, the reactivity of allyl alcohol is much lower than that of the carboxylic acid ester.

Another problem arises when allyl alcohol is used as the allyl source. Namely, the phosphine as the ligand is oxidized with the oxygen atom of allyl alcohol with advance of the reaction.

Atkins et al. synthesized allyldiethylamine from allyl alcohol and diethylamine in a catalyst system formed by using Pd(CH$_2$COCH$_2$COCH$_3$)$_2$ as the starting complex and adding triphenylphosphine in an amount equimolar tion of an allyl type amine, which comprises reacting an allyl type alcohol represented by the following formula:

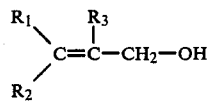

wherein R$_1$, R$_2$, and R$_3$ independently stand for a hydrogen atom, an aliphatic hydrocarbon group or alicyclic hydrocarbon having 1 to 8 carbon atoms, or an aromatic hydrocarbon group, with at least one member selected from the group consisting of ammonia, a primary amine and a secondary amine in the presence of a palladium compound and a multidentate phosphorus compound.

As the palladium compound valuably used in the present invention, there can be mentioned inorganic salts such as PdCl₂, PdBr₂, PdI₂, Pd(OCOCH₃)₂, Pd(CH₂COCH₂COCH₃)₂, K₂PdCl₄, K₂PdCl₆ and K₂Pd(NO₃)₄, organic ligand complexes such as PdCl₂(C₂H₄)₂, Pd(π-C₃H₅)₂, PdCl₂(C₈H₁₂) and Pd(C₈H₁₂)₂, N-coordination complexes such as PdCl₂(NH₃)₂, PdCl₂[N(C₂H₅)₃]₂ and Pd(NO₃)₂(NH₃)₆, and complexes having a trivalent phosphine compound as the ligand, such as Pd[P(CH₃)₃]₄, Pd[P(C₂H₅)₃]₄, Pd[P(n-C₃H₇)₃]₄, Pd[P(iso-C₃H₇)₃]₄, Pd[P(n-C₄H₉)₃]₄, Pd[P(C₆H₅)₃]₄, PdCO₂[P(C₆H₅)₃]₂, Pd(C₂H₄)[P(C₆H₅)₃]₂, PdCl₂[P(C₆H₅)₃]₂, PdCl₂[P(n-C₄H₉)₃]₂, PdBr₂[P(C₆H₅)₃]₂, PdBr₂[P(n-C₄H₉)₃]₂, PdCl₂[P(OCH₃)₃]₂, PdI₂[P(OCH₃)₃]₂ and PdCl(C₆H₅)[P(C₆H₅)₃]₂. Of course, palladium compounds that can be used in the present invention are not limited to those exemplified above.

As the multidentate phosphorus compound, there can be mentioned bidentate compounds represented by the following general formula:

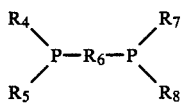

wherein R₄, R₅, R₇ and R₈ stand for an aliphatic hydrocarbon group, aromatic hydrocarbon group or alicyclic hydrocarbon group having 1 to 20 carbon atoms, and R₆ stands for a divalent hydrocarbon group.

As specific examples of the compound of this type, there can be mentioned (CH₃)₂PCH₂P(CH₃)₂, (C₂H₅)₂P(CH₂)P(C₂H₅)₂, (C₆H₅)₂P(CH₂)₂P(C₆H₅)₂, (n-C₄H₉)₂P(CH₂)₂P(n-C₄H₉)₂, (t-C₄H₉)₂P(CH₂)₂P(t-C₄H₉)₂, (C₆H₅)₂P(CH₂)₃P(C₆H₅)₂, (n-C₄H₉)₂P(CH₂)₃P(n-C₄H₉)₂, (C₆H₅)₂P(CH₂)₄P(C₆H₅)₂, (C₂H₅)₂P(CH₂)₄P(C₂H₅)₂, (C₆H₅)₂P(CH₂)₅P(C₆H₅)₂, (n-C₄H₉)₂P(CH₂)₅P(n-C₄H₉)₂ and (C₂H₅)₂P(CH₂)₅P(C₂H₅)₂. Of these compounds, 1,4-bis(diphenyl-phosphino)-butane and 1,3-bis-(diphenylphosphino)-propane are particularly preferred. Phosphorus compounds that can be used are not limited to those exemplified above.

As examples of the primary amine that can be valuably used in the present invention, there can be mentioned aliphatic linear and cyclic amines such as CH₃NH₂, C₂H₅NH₂, C₃H₅NH₂, n-C₃H₇NH₂, iso-C₃H₇NH₂, n-C₄H₂NH₂, iso-C₄H₉NH₂, t-C₄H₉NH₂, n-C₅H₉NH₂, n-C₅H₁₁NH₂, iso-C₅H₁₁NH₂, n-C₆H₁₃NH₂, n-C₈H₁₇NH₂ and cyclo-C₅H₁₁NH₂, aromatic amines such as C₆H₅NH₂, C₆H₅CH₂NH₂, o-CH₃C₆H₄NH₂, m-CH₃C₆H₄NH₂, p-CH₃C₆H₄NH₂, o-CH₃OC₆H₄NH₂, m-CH₃OC₆H₄NH₂, p-CH₃OC₆H₄NH₂, o-ClC₆H₄NH₂, m-ClC₆H₄NH₂, p-ClC₆H₄NH₂, 2,6-(CH₃)₂C₆H₃NH₂ and 2,4,6-(CH₃)₃C₆H₂NH₂, and aliphatic and aromatic diamines such as NH₂CH₂CH₂NH₂, NH₂CH₂CH₂CH₂NH₂, NH₂CH₂CH₂CH₂CH₂CH₂NH₂, NH₂CH₂CH₂CH₂CH₂CH₂CH₂CH₂NH₂, o-NH₂C₆H₄NH₂, m-NH₂C₆H₄NH₂ and p-NH₂C₆H₄NH₂. Of, course, primary amines that can be used in the present invention are not limited to those exemplified above.

As the secondary amine, there can be mentioned aliphatic linear and cyclic amines such as (CH₃)₂NH, (C₂H₅)₂NH, (C₃H₅)₂NH, (n-C₃H₇)₂NH, (n-C₄H₉)₂NH, (iso-C₄H₉)₂NH, (t-C₄H₉)₂NH, (n-C₅H₉)₂NH, (n-C₅H₁₁)₂NH, (n-C₆H₁₃)₂NH, (cyclo-C₆H₁₁)(CH₃)NH, (CH₃)(C₂H₅)NH and (C₂H₅)(C₃H₅)NH aromatic amines such as (C₆H₅)(CH₃)NH, (C₆H₅CH₂)(CH₃)NH, (o-CH₃C₆H₄)(CH₃)NH, (m-CH₃C₆H₄)(CH₃)NH, (p-CH₃C₆H₄)(CH₃)NH, (o-CH₃OC₆H₄)(CH₃)NH and (C₆H₅)₂NH, and heterocyclic amines such as

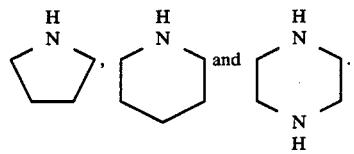

The reaction of the process of the present invention is advantageously advanced if an alkali is added. As the alkali that can be used, there can be mentioned ammonium hydroxide salts such as (CH₃)₄NOH, (C₂H₅)₄NOH, (C₃H₅)₄NOH, (n-C₃H₇)₄NOH, (iso-C₃H₇)₄NOH, (n-C₄H₉)₄NOH, (iso-C₄H₉)₄NOH, (t-C₄H₉)₄NOH, (CH₃)(n-C₄H₉)₃NOH, (C₂H₅)₂(n-C₃H₇)₂NOH and (C₆H₅CH₂)(CH₃)₃NOH, alkali metal compounds such as NaOH, KOH, LiOH, NaH, KH, LiH, NaBH₄ and LiAlH₄, organic alkali metal compounds such as CH₃Li, C₂H₅Li, n-C₃H₇Li and n-C₄H₇Li, alkali metal alkoxides such as CH₃ONa, and C₂H₅ONa, n-C₄H₉ONa, C₂H₅OLi and C₂H₅OK, alkali metal salts of phenols such as C₆H₅ONa, C₆H₅OK, C₆H₅OLi, o-CH₃C₆H₄ONa, n-CH₃C₆H₄ONa, p-CH₃C₆H₄ONa, o-CH₃C₆H₄OK, m-CH₃C₆H₄OK and p-CH₃C₆H₄OK. Of them, tetrabutylammonium hydroxide and tertiary butylammonium hydroxide are especially preferred. Of course, alkalis that can be added in the present invention are not limited to those mentioned above.

It is preferred that the alkali be added in such an amount that the molar ratio to the palladium metal of the palladium compound be from 1 to 500, especially from 1 to 200.

In the process of the present invention, it is preferred that the above-mentioned combination catalyst comprising the palladium compound and multidentate phosphorus compound be used in an amount of 1/10 to 1/100,000 mole, especially 1/50 to 1/20,000 mole, per mole of the allyl type alcohol. It also is preferred that the multidentate phosphorus compound be used in such an amount that the molar ratio to the palladium metal of the palladium compound is from 1 to 100, especially from 1 to 20. In the case where a multidentate phosphorus compound is contained in the palladium compound, it sometimes happens that a multidentate compound need not be further added. In the present invention, use of a multidentate compound is indispensable, but the presence of a monodentate phosphorus compound is permissible.

In the process of the present invention, it is preferred that ammonia or the amine be used in such an amount that the molar ratio to the allyl type alcohol is from 1/100 to 100, especially from 1/10 to 10, particularly 1 to 5. The reaction between the allyl type alcohol and ammonia or the amine is carried out at 0° to 200° C., preferably 30° to 150° C., especially 60° to 150° C., especially 60° to 150° C.

The process of the present invention can be carried out in the presence or absence of a solvent. As examples of the solvent valuably used in the present invention, there can be mentioned alcohols such as methanol, ethanol, n-propyl alcohol, isopropyl alcohol, n-butyl alcohol, isobutyl alcohol, t-butyl alcohol, ethylene glycol and propylene glycol, aromatic and aliphatic hydrocarbons such as benzene, toluene and hexane, nitriles such as acetonitrile, benzonitrile, acrylonitrile and adiponitrile, halogenated hydrocarbons such as chlorobenzene, dichlorobenzene, tetrachloromethane, chloroform and dichloromethane, ethers such as dibutyl ether, dioxane, diethylene glycol dimethyl ether and triethylene glycol dimethyl ether, tertiary amines such as triethylamine, tripropylamine, tributylamine and N,N-dimethylaniline, and water. Of them, propylene glycol and 1,4-butanediol are particularly preferred. Solvents that can be used in the present invention are not limited to those exemplified above.

According to the process of the present invention, an allyl type amine can be prepared in a good yield without formation of a salt as a by-product by using an allyl type alcohol and ammonia or a primary amine and/or a secondary amine. Namely, an allyl type amine can be prepared at a high efficiency and a low cost according to the process of the present invention.

The present invention will now be described in detail with reference to the following examples that by no means limit the scope of the invention.

EXAMPLE 1

A pressure vessel of glass having an inner capacity of 100 ml was charged with 15.3 mg (0.05 millimole) of $Pd(CH_2COCH_2COCH_3)_2$ and 42.5 mg (0.10 millimole) of 1,4-bis(diphenylphosphino)butane, and the inner atmosphere was replaced by nitrogen. Then, 4.9 g of propylene glycol, 8.4 g (145 millimoles) of allyl alcohol and 3.6 g of water were added to the charge in the vessel, and 4.0 g (235 millimoles) of ammonia was introduced into the vessel and reaction was carried out at 110° C. for 4 hours with stirring. As the products, there were obtained 0.91 g (15.9 millimoles) of monoallylamine, 1.65 g (17.0 millimoles) of diallylamine and 1.81 g (13.2 millimoles) of triallylamine. The conversion based on allyl alcohol was 62.8% and diallyl ether was formed in an amount of 0.4% as a by-product. Incidentally, confirmation of the structures of the products and determination were carried out by GC, LC, NMR, GCMS and the like.

EXAMPLE 2

The operation was carried out in a manner similar to one described in Example 1. As the palladium compound, 15.3 mg (0.05 millimole) of $Pd(CH_2COCH_2COCH_3)_2$ was used, and as the multidentate phosphorus compound, 41.2 mg (0.10 millimole) of 1,3-bis(diphenylphosphino)propane was used. As the solvent, 5.1 g of propylene glycol was used, and after the addition of 8.4 g (145 millimoles) of allyl alcohol, 4.0 g (235 millimoles) of ammonia was introduced and reaction was carried out at 110° C. for 4 hours. As the products, there were obtained 0.85 g (14.8 millimoles) of monoallylamine, 1.79 g (18.4 millimoles) of diallylamine and 2.33 g (17.0 millimoles) of triallylamine. The conversion based on allyl alcohol was 73.5% and the selectivity was 98.9%.

EXAMPLE 3

To 1.8 mg (0.01 millimole) of $PdCl_2$ was added 8.5 mg (0.02 millimole) of 1,4-bis(diphenylphosphino)butane, and 5.0 g of 1,3-propane-diol and 3.6 g of water were added and reaction between 8.4 g (145 millimoles) of allyl alcohol and 3.2 g (188 millimoles) of ammonia was carried out at 110° C. with stirring for 2 hours. As the products, there were obtained 0.26 g (4.6 millimoles) of monoallylamine, 0.53 g (5.4 millimoles) of diallylamine 0.63 g (4.6 millimoles) of triallylamine. The conversion based on allyl alcohol was 21.5% and the selectivity was 96.8%.

EXAMPLE 4

To 1.8 mg (0.01 millimole) of $PdCl_2$ was added 8.5 mg (0.02 millimole) of 1,4-bis(diphenylphosphino)butane, and 5.0 g of 1,3-propane-diol, 3.6 mg of water and 9.1 mg (0.01 millimole) of tetramethyl hydroxide were added and reaction between 8.4 g (145 millimoles) of allyl alcohol and 4.6 g (271 millimoles) of ammonia was carried out at 110° C. with stirring for 2 hours. As the products, there were obtained 0.20 g (3.5 millimoles) of monoallylamine, 0.78 (8.0 millimoles) of diallylamine and 0.92 g (6.7 millimoles) of triallylamine. The conversion based on allyl alcohol was 29.8%, and the selectivity was 91.7%.

EXAMPLE 5

To 11.5 mg (0.01 millimole) of $Pd[P(C_6H_5)_3]_4$ was added 8.2 mg (0.02 millimole) of 1,3-bis(diphenylphosphino)propane, and 5 g of diethylene glycol dimethyl ether and 4 mg (0.1 millimole) of sodium hydroxide were added and reaction between 7.2 g (100 millimoles) of methallyl alcohol and 4.0 g (235 millimoles) of ammonia was carried out 100° C. for 4 hours with stirring. As the products, there were obtained 0.34 g (4.8 millimoles) of monomethallyl amine, 0.78 g (6.2 millimoles) of dimethallyl amine and 1.45 g (8.1 millimoles) of trimethallyl amine. The conversion based on methallyl alcohol was 44.7%, and the selectivity was 92.8%.

EXAMPLE 6

To 12.2 mg (0.04 millimole) of $Pd(CH_2COCH_2COCH_3)_2$ was added 42.6 mg (0.10 millimole) of 1,4-bis(dibutylphosphino)butane, and 5.0 g of 1,4-butanediol was added and reaction between 8.4 g (182 millimoles) of allyl alcohol and 3.1 g (182 millimoles) of ammonia was carried out at 120° C. for 2 hours with stirring. As the products, there were obtained 0.91 (16.0 millimoles) of monoallylamine, 1.85 g (19.1 millimoles) of diallylamine and 2.35 g (17.2 millimoles) of triallylamine. The conversion based on allylalcohol was 74.3%, and the selectivity was 98.2%.

EXAMPLES 7 THROUGH 19

In a solvent comprising 5 g of propylene glycol and 3.6 g of water, 3.0 g (52.5 millimoles) of monoallylamine was reacted with 8.4 g (144.6 millimoles) of allyl alcohol at 110° C. for 2 hours in the presence of a catalyst and alkali shown in Table 1. The composition of the obtained products and the conversion of allyl alcohol are shown in Table 2.

TABLE 1

| Example No. | Catalyst palladium compound | phosphorus compound | Alkali |
|---|---|---|---|
| 7 | $Pd(CH_2COCH_2COCH_3)_2$ 12.2 mg (0.04 millimole) | $P(C_6H_5)_3$ 94.3 mg (0.36 millimole) | not added |
| 8 | $Pd(CH_2COCH_2COCH_3)_2$ 12.2 mg (0.04 millimole) | $P(n-C_4H_9)_3$ 50.0 mg (0.25 millimole) | not added |
| 9 | $Pd(CH_2COCH_2COCH_3)_2$ 12.2 mg (0.04 millimole) | DPPB 25.6 mg (0.06 millimole) | not added |
| 10 | $Pd(CH_2COCH_2COCH_3)_2$ 3.1 mg (0.01 millimole) | DPPB 8.5 mg (0.02 millimole) | not added |
| 11 | $Pd(CH_2COCH_2COCH_3)_2$ 3.1 mg (0.01 millimole) | DPPB 8.5 mg (0.02 millimole) | NaOH 20.0 mg (0.5 millimole) |
| 12 | $Pd(CH_2COCH_2COCH_3)_2$ 3.1 mg (0.01 millimole) | DPPB 8.5 mg (0.02 millimole) | TBAHO (0.5 millimole) |
| 13 | $Pd[P(C_6H_5)_3]_4$ 46.0 mg (0.04 millimole) | not added | not added |
| 14 | $Pd[P(C_6H_5)_3]_4$ 46.0 mg (0.04 millimole) | $P(C_5H_5)_3$ 52.4 mg (0.2 millimole) | not added |
| 15 | $Pd[P(C_6H_5)_3]_4$ 46.0 mg (0.04 millimole) | $P(C_2H_5)_3$ 12.0 mg (0.07 millimole) | not added |
| 16 | $Pd[P(C_6H_5)_3]_4$ 46.0 mg (0.04 millimole) | $P(n-C_4H_4)_3$ 26.4 mg (0.13 millimole) | not added |
| 17 | $Pd[P(C_6H_5)_3]_4$ 46.0 mg (0.04 millimole) | DPPE 24.0 mg (0.06 millimole) | not added |
| 18 | $Pd[P(C_6H_5)_3]_4$ 11.5 mg (0.01 millimole) | DPPB 8.5 mg (0.02 millimole) | not added |
| 19 | $Pd[P(C_6H_5)_3]_4$ 11.5 mg (0.01 millimole) | DPPB 8.5 mg (0.02 millimole) | NaOH 20.0 mg (0.5 millimole) |

Incidentally, in Table 1, DPPB indicates 1,4-bis(diphenylphosphino)butane, DPPE indicates 1,2-bis(diphenylphosphino)ethane, and TBAHO indicates tetrabutylammonium hydroxide.

TABLE 2

| Example No. | Diallylamine, g (millimoles) | Triallylamine, g (millimoles) | Diallyl Ether, g (millimoles) | Conversion (%) |
|---|---|---|---|---|
| 7 | 0.81 (8.3) | 0.68 (5.0) | 0.10 (1.0) | 6.3 |
| 8 | 0.87 (9.0) | 0.99 (7.2) | 0.10 (1.0) | 16.8 |
| 9 | 1.14 (11.8) | 3.48 (25.4) | 0.32 (3.3) | 35.6 |
| 10 | 1.40 (14.4) | 1.76 (12.8) | 0.10 (1.0) | 13.0 |
| 11 | 0.73 (7.5) | 4.00 (29.2) | 0.42 (4.3) | 51.8 |
| 12 | 0.50 (5.2) | 3.14 (22.9) | 0.38 (3.9) | 44.0 |
| 13 | 0.96 (9.9) | 0.48 (3.5) | 0.10 (1.0) | 6.8 |
| 14 | 0.70 (7.2) | 0.43 (3.1) | 0.10 (1.0) | 7.6 |
| 15 | 1.00 (10.3) | 1.26 (9.2) | 0.13 (1.3) | 16.8 |
| 16 | 0.77 (7.9) | 0.95 (6.9) | 0.12 (1.2) | 17.1 |
| 17 | 9.98 (10.1) | 3.68 (26.9) | 0.40 (4.1) | 45.9 |
| 18 | 0.96 (9.9) | 0.48 (3.5) | 0.12 (1.2) | 9.0 |
| 19 | 0.85 (8.8) | 1.43 (10.4) | 0.28 (2.9) | 26.9 |

EXAMPLES 20 AND 21

In a solvent comprising 5 g of propylene glycol and 3.6 g of water, 3.79 g (51.8 millimoles) of diethylamine was reacted with 8.4 g (144.6 millimoles) of allyl alcohol at 110° C. for 1 hour in the presence of a catalyst and alkali shown in Table 3. The composition of the obtained products and the conversion of allyl alcohol are shown in Table 4.

TABLE 3

| Example No. | Catalyst palladium compound | phosphorus compound | Alkali |
|---|---|---|---|
| 20 | $Pd(CH_2COCH_2COCH_3)_2$ 3.1 mg (0.01 millimole) | DPPB 8.5 mg (0.02 millimole) | not added |
| 21 | $Pd(CH_2COOCH_2COCH_3)_2$ 3.1 mg (0.01 millimole) | DPPB 8.5 mg (0.02 millimole) | NaOH 20.0 mg (0.5 millimole) |

Incidentally, in Table 3, DPPB indicates 1,4-bis(diphenylphosphino)butane.

TABLE 4

| Example No. | Allyldiethylamine, g (millimoles) | Diallyl Ether, g (millimoles) | Conversion (%) |
|---|---|---|---|
| 20 | 1.68 (14.9) | 0.10 (1.0) | 11.7 |
| 21 | 5.27 (46.6) | 0.12 (1.2) | 33.7 |

EXAMPLE 22

A composition comprising 3.1 mg (0.01 millimole) of $Pd(CH_2COCH_2COCH_3)_2$, 8.5 mg (0.02 millimole) of 1,4-bis(diphenylphosphino)butane, 130 mg (0.50 millimole) of TBAHO, 5 ml of propylene glycol, 3.6 ml of water, 8.41 g (144.8 millimoles) of allyl alcohol and 5.57 g (52.0 millimoles) of N-methylaniline was subjected to reaction at 110° C. for 2 hours.

The conversion of allyl alcohol was 36.4%, and the product comprised 2.69 g (25.1 millimoles) of N-methyl-N-allylaniline and 1.35 g (13.8 millimoles) of diallyl ether.

EXAMPLE 23

A composition comprising 15.3 mg (0.05 millimole) of $Pd(CH_2COCH_2COCH_3)_2$, 41.2 mg (0.10 millimole) of 1,3-bis(diphenylphosphino)propane, 130 mg (0.50 millimole) of TBAHO, 10 ml of 1,4-butane-diol, 8.40 g (144.8 millimoles) of allyl alcohol and 3.79 g (51.8 millimoles) of diethylamine was subjected to reaction at 110° C. for 2 hours.

The conversion of allyl alcohol was 34.8%, and the product comprised 5.2 g (46.0 millimoles) of allyldiethylamine and 0.1 g (1.0 millimole) of diallyl ether.

EXAMPLE 24

A composition comprising 3.5 mg (0.02 millimole) of PdCl$_2$, 25.6 mg (0.06 millimole) of 1,4-bis(diphenylphosphino)butane, 45.5 mg (0.50 millimole) of TMAHO, 5 ml of 1,3-butane-diol, 10.8 g (150.0 millimoles) of methallyl alcohol and 3.80 g (52.1 millimoles) of diethylamine was subjected to reaction at 100° C. for 4 hours.

The conversion of methallyl alcohol was 32.3%, and the product comprised 5.9 g (46.5 millimoles) of methallyldiethylamine and 0.1 g (1.0 millimole) of dimethallyl ether.

EXAMPLE 25

A composition comprising 4.4 mg (0.02 millimole) of Pd(OCOCH$_3$)$_2$, 17.1 mg (0.04 millimole) of 1,4-bis-(diphenylphosphino)-butane, 68 mg (0.75 millimole) of tetramethylammonium hydroxide, 5 ml of propylene glycol, 8.29 g (142.7 millimoles) of allyl alcohol and 5.26 g (54.1 millimoles) of diallylamine was subjected to reaction at 110° C. for 2 hours.

The conversion of allyl alcohol was 42.1%, and the product comprised 7.31 g (53.3 millimoles) of triallylamine and 0.62 g of (6.4 millimoles) of diallyl ether.

EXAMPLE 26

A composition comprising 6.1 mg (0.02 millimole) of Pd(CH$_2$COCH$_2$COCH$_3$)$_2$, 25.6 mg (0.06 millimole) of 1,4-bis-(diphenyl-phosphino)-butane, 13 mg (0.5 millimole) of tertiary butylammonium hydroxide, 5 ml of propylene glycol, 8.33 g (143.4 millimoles) of allyl alcohol, 1.23 g (72.4 millimoles) of ammonia and 1.50 g (26.3 millimoles) of monoallylamine was subjected to reaction at 110° C. for 2 hours.

The product comprised 0.42 g (4.3 millimoles) of diallylamine, 4.40 g (32.1 millimoles) of triallylamine and 0.25 g of (2.5 millimoles) of diallyl ether.

EXAMPLE 27

A composition comprising 4.4 mg (0.02 millimole) of Pd(OCOCH$_3$)$_2$, 25.6 mg (0.0 g millimole) of 1,4-bis-(diphenyl-phosphino)-butane, 68 mg (0.75 millimole) of tetramethylammonium hydroxide, 5 ml of propylene glycol, 8.32 g (143.3 millimoles) of allyl alcohol and 2.23 g (49.4 millimoles) of dimethylamine was subjected to reaction at 110° C. for 2 hours.

The product comprised 3.90 g (45.8 millimoles) of allydimethylamine.

We claim:

1. A process for the preparation of an allyl amine, which comprises reacting an allyl alcohol represented by the following formula (I):

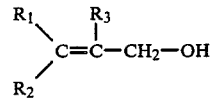

wherein R$_1$, R$_2$ and R$_3$ independently represent a hydrogen atom or an aliphatic hydrocarbon group having 1 to 8 carbon atoms with at least one member selected from the group consisting of ammonia, a primary amine and a secondary amine in the presence of a palladium compound and a multidentate phosphorus compound.

2. A process according to claim 1, wherein the allyl alcohol of the formula (I) is allyl alcohol.

3. A process according to claim 1, wherein the primary amine is monoallylamine.

4. A process according to claim 1, wherein the secondary amine is selected from the group consisting of diallylamine and dimethylamine.

5. A process according to claim 1, wherein the reaction is carried out in the presence of an alkali, and the alkali is present in such an amount that the molar ratio to the palladium metal of the palladium compound is from 1 to 200.

6. A process according to claim 5, wherein the alkali is an organic base selected from the group consisting of tetramethylammonium hydroxide and tetrabutylammonium hydroxide.

7. A process according to claim 1, wherein the multidentate phosphorus compound is present in such an amount that the molar ratio to the palladium metal of the palladium compound is from 1 to 20.

8. A process according to claim 1, wherein ammonia or the amine is present in such an amount that the molar ratio to the allyl type alcohol is from 1 to 5 and the reaction is carried out at a temperature of 60° to 150° C.

9. A process according to claim 1, wherein the reaction is carried out in the presence of a solvent, and the solvent is selected from the group consisting of propylene glycol and 1,4-butanediol.

10. A process according to claim 1, wherein the multidentate phosphorus compound is a bidentate phosphorus compound represented by the formula (II):

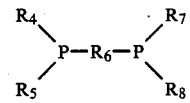

wherein R$_4$, R$_5$, R$_7$ and R$_8$ independently represent an aliphatic hydrocarbon group, each having 1 to 20 carbon atoms or a phenyl group, and R$_6$ represents a divalent hydrocarbon group having 1 to 5 carbon atoms.

11. A process according to claim 10, wherein the bidentate phosphorus compound is selected from the group consisting of 1,4-bis(diphenyl-phosphino)-butane and 1,3-bis-(diphenyl-phosphino)-propane.

* * * * *